United States Patent
Kroll

(10) Patent No.: US 6,549,806 B1
(45) Date of Patent: Apr. 15, 2003

(54) IMPLANTABLE DUAL SITE CARDIAC STIMULATION DEVICE HAVING INDEPENDENT AUTOMATIC CAPTURE CAPABILITY

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 293 days.

(21) Appl. No.: 09/684,625

(22) Filed: Oct. 5, 2000

Related U.S. Application Data

(60) Provisional application No. 60/204,088, filed on May 15, 2000.

(51) Int. Cl.[7] .................................................. A61N 1/37
(52) U.S. Cl. ........................................................ 607/27
(58) Field of Search ................................ 607/9, 11, 27, 607/28, 29

(56) References Cited

U.S. PATENT DOCUMENTS

| | | | | |
|---|---|---|---|---|
| 4,712,555 A | | 12/1987 | Thornander et al. | 128/419 PG |
| 4,788,980 A | | 12/1988 | Mann et al. | 128/419 PG |
| 4,940,052 A | | 7/1990 | Mann et al. | 128/419 PG |
| 4,944,298 A | | 7/1990 | Sholder | 128/419 PG |
| 4,979,507 A | | 12/1990 | Heinz et al. | 128/419 PG |
| 5,447,525 A | | 9/1995 | Powell et al. | 607/28 |
| 5,601,615 A | * | 2/1997 | Markowitz et al. | 607/28 |
| 5,697,956 A | | 12/1997 | Bornizn | 607/28 |
| 5,713,933 A | * | 2/1998 | Condie et al. | 607/28 |
| 5,800,465 A | * | 9/1998 | Thompson et al. | 607/122 |
| 6,148,234 A | * | 11/2000 | Struble | 607/11 |

OTHER PUBLICATIONS

Pacesetter®, "AFFINITY™ DR Model 5330 L/R, Dual–Chamber Pulse Generator with AUTOCAPTURE™ Pacing System", 1998 St. Jude Medical, Inc.

* cited by examiner

*Primary Examiner*—Jeffrey R. Jastrzab

(57) ABSTRACT

An improved device and method for automatically determining threshold detection and maintaining capture in a multiple, e.g., dual, site cardiac stimulation device. When multiple site stimulation is used, e.g., for treatment of congestive heart failure (CHF) or the like, the threshold stimulation energy level at each of the sites will typically be different and, in the case of a lead implanted in the coronary sinus (CS), threshold stimulation energy level may be significantly different, e.g., 50 times greater or more. Accordingly, embodiments of the present invention independently maintain capture for each site and, preferably, independently determine the threshold for each site. In a significant aspect of the present invention, a preferred device periodically determines the chronaxie and rheobase corresponding to a strength-duration curve for each site and sets initial controlled energy levels accordingly. Once each initial controlled energy level is determined, which preferably includes a safety margin, the controlled energy level is increased when a loss-of-capture criteria is met. Furthermore, power expended from the battery is minimized since each site is individually optimized.

29 Claims, 5 Drawing Sheets

IMPLANTABLE DUAL SITE CARDIAC STIMULATION DEVICE HAVING INDEPENDENT AUTOMATIC CAPTURE CAPABILITY

This application claims the benefit of U.S. Provisional Application No. 60/204,088, filed May 15, 2000.

FIELD OF THE INVENTION

The present invention is generally directed to an implantable medical device, e.g., a cardiac stimulation device, and is particularly directed to an automatic capture/threshold pacing method for use in such a device.

BACKGROUND OF THE INVENTION

Implantable cardiac stimulation devices are well known in the art. They include implantable pacemakers which provide stimulation pulses to cause a heart, which would normally beat too slowly or at an irregular rate, to beat at a controlled normal rate. They also include defibrillators which detect when the atria and/or the ventricles of the heart are in fibrillation or in a pathologic rapid rhythm and then apply cardioverting or defibrillating electrical energy to the heart to restore and maintain the heart in a normal rhythm. Implantable cardiac stimulation devices may also include the combined functions of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation pulses when they are needed and inhibit the delivery of cardiac stimulation pulses at other times. This inhibition accomplishes two primary functions. Firstly, when the heart is intrinsically stimulated, the patient's hemodynamics are generally improved. Secondly, inhibiting the delivery of a cardiac stimulation pulse reduces the overall battery current drain and therefore extends the life of the device battery. Extending the battery life, will therefore delay the need to explant and replace the cardiac stimulation device due to an expended battery. Generally, the circuitry used in implantable cardiac stimulation devices has been significantly improved since their introduction such that the major limitation of the battery life is related primarily to the number and amplitude of the stimulation pulses. Accordingly, it is preferable to minimize the number of pulses delivered by using this inhibition function and to minimize the amplitude of the pulses when it is clinically appropriate.

It is well known that the amplitude of a pulse that will reliably stimulate a patient's heart, i.e., its threshold value, will change over time after implantation and will vary with the patient's activity level and other physiological factors. To accommodate for these changes, pacemakers may be programmed to deliver a pulse at an amplitude well above an observed threshold value. To avoid wasting battery energy, techniques were developed to automatically adjust the pulse amplitude to accommodate for these long- and short-term physiological changes. For example, an existing device, the Affinity® DR, Model 5330 L/R Dual-Chamber Pulse Generator, manufactured by the assignee of the present invention, an AutoCapture™ pacing system is provided. The User's Manual, ©1998 St. Jude Medical, which describes this technique is incorporated herein by reference. In this system, the threshold amplitude level is automatically determined for a predetermined duration level in a threshold search routine and capture is maintained by a capture verification routine. Once the threshold search routine has determined a pulse amplitude that will reliably stimulate, i.e., capture, the patient's heart, the capture verification routine monitors signals from the patient's heart to identify pulses that do not stimulate the patient's heart (indicating a loss-of-capture). Should a loss-of-capture (LOC) occur, the capture verification routine will generate a large amplitude (e.g., 4.5 volt) backup pulse shortly after (typically within 80–100 ms) the original (primary) stimulation pulse. This capture verification occurs on a pulse-by-pulse basis and thus, the patient's heart will not miss a beat. However, while capture verification ensures the patient's safety, the delivery of two stimulation pulses (with the second stimulation pulse typically being much larger in amplitude) is potentially wasteful of a limited resource, that is the battery capacity. To avoid this condition, the existing device monitors for the occurrence of two consecutive loss-of-capture events and only increases the amplitude of the primary stimulation pulse when two consecutive loss-of-capture (LOC) events occur, i.e., according to a loss-of-capture criteria. This procedure is repeated, if necessary, until two consecutive pulses are captured, at which time a threshold search routine is triggered. The threshold search routine decreases the primary pulse amplitude until capture is lost on two consecutive pulses and then, in a similar manner to that previously described, increases the pulse amplitude until two consecutive captures are detected. The value of the pulse amplitude when capture thus occurs is defined as the capture threshold. The primary pulse amplitude is then increased by a safety margin value to ensure a primary pulse whose amplitude will exceed the threshold value and thus reliably capture the patient's heart without the need for frequent backup pulses. In a copending, commonly-assigned U.S. patent application Ser. No. 09/483,908, filed Jan. 18, 2000, entitled "An Implantable Cardiac Stimulation Device Having Autocapture/Autothreshold Capability," improved loss-of-capture criteria are disclosed which are based upon X out of the last Y beats, where Y is greater than 2 and X is less than Y. U.S. patent application Ser. No. 09/483,908 is incorporated herein by reference in its entirety.

To treat certain heart conditions, e.g., congestive heart failure (CHF), pacing is done on both the right and left sides of the patient's heart, e.g., at the right and left ventricles. Typically, while stimulation of the right ventricle occurs via a lead implanted in the right ventricular apex, stimulation of the left ventricle is accomplished through a lead implanted within the coronary sinus (CS). It is critical to ensure that stimulation pulses delivered through the left side (CS) lead are captured by the patient's heart. The energy used for each pulse is a function of the amplitude level (i.e., voltage or current) and the duration of the delivered pulse as shown in the equation:

$$E=(V^2*d)/R$$

where V is the amplitude of the stimulation pulse, d is its duration and R is the lead impedance.

Tissue in the coronary sinus may have a threshold as high as 6.0 volts and, therefore may require a pulse having at least a 6.0 volt amplitude and a pulse width of 1.0 milliseconds for capture to be obtained. This threshold is significantly higher than what typically exists on the right side of the patient's heart since the CS stimulation voltage must "reach through" the vein tissue before it gets to the active myocardial tissue. Additionally, a larger chronaxie may result from the lead's larger surface area ring electrode which is typically used for a CS lead. Accordingly, by applying the above equation, a pulse energy level as high as 72 microjoules is determined (assuming a typical lead impedance of 500 ohms). This is a pulse energy level that could rapidly deplete the device battery. By contrast, pacing in the right ventricular apex (RVA), which has an exemplary 1.50 volt threshold and using a 500 microsecond pulse width through a 1000 ohm lead impedance gives rise to a pulse energy level of 1.1 microjoules which is significantly lower than the exemplary pulse energy level determined for the CS lead. With such a large pulse energy difference between the stimulation sites, it is significant that the left side pulse energy level not dictate the right side pulse energy level which would result in almost a 50% waste of power. Furthermore, if the right side energy level dictated the left side energy level, the left side stimulation pulses would not be able to capture the heart. Furthermore, with multiple sites, the chronaxie, rheobase and impedance values are different and may change with time. Accordingly, any solution based upon a relationship between the right and left side stimulation requirements would be time limited. It is not believed that these dual site complications have been addressed in the prior art.

Furthermore, U.S. Pat. No. 5,697,956 to Bornzin, which is incorporated herein by reference, recognized that while the selection of stimulation energy levels was ideally related to the strength-duration curve for the patient's cardiac tissue, optimal increases in energy levels should also take into account the battery voltage when voltage multipliers (e.g., voltage doublers or triplers) are necessary to achieve a desired stimulation voltage. Accordingly, Bornzin showed an energy curve (see FIG. 7 of Bornzin) that selectively increased either amplitude or duration to increase the stimulation energy level while avoiding use of the voltage multipliers when possible. However, Bornzin did not address these issues in a dual site environment.

Therefore what is needed is a system that can independently and optimally determine the threshold energy for stimulation pulses for the right and left sides of the patient's heart and therefore minimize battery depletion while ensuring capture at each of the pacing sites.

SUMMARY OF THE INVENTION

The present invention provides an improved device and method for automatically determining threshold detection and maintaining capture in a multiple, e.g., dual, site cardiac stimulation device. When multiple site stimulation is used, e.g., for treatment of congestive heart failure or the like, the threshold stimulation energy level at each of the sites will typically be different and, in the case of a lead implanted in the coronary sinus (CS), threshold stimulation energy level may be significantly different, e.g., 50 times greater or more. Accordingly, embodiments of the present invention independently maintain capture for each site and, preferably, independently determine the threshold for each site. In a significant aspect of the present invention, a preferred device periodically determines the chronaxie and rheobase corresponding to a strength-duration curve for each site and sets initial controlled energy levels accordingly. Once each initial controlled energy level is determined, which preferably includes a safety margin, the controlled energy level is increased when a loss-of-capture criteria is met. Furthermore, power expended from the battery is minimized since each site is individually optimized.

Accordingly, a preferred implantable stimulation device is connected to at least two electrodes implanted in a patient's heart where a first electrode is positioned to stimulate a chamber in the right side of the patient's heart and the second electrode is positioned to stimulate a corresponding chamber in the left side of the patient's heart. Periodically, the implantable stimulation device determines strength-duration curves for each side of the patient's heart. Using the determined strength-duration curves, the stimulation device then determines controlled energy levels for each side of the patient's heart that are based upon their respective strength-duration curves.

Furthermore, once controlled energy levels have been individually determined for each (i.e., the right and left) side of the patient's heart, capture is individually monitored and maintained for each side. For example, if a first controlled energy level, which is used to stimulate the right side of the patient's heart, fails to generate an evoked response, the first controlled energy level is increased. Similarly and independently, a second controlled energy level is used to stimulate the left side of the patient's heart and the second controlled energy level is increased if an evoked response is absent.

In a further aspect of the present invention, a preferred device takes into account potential losses due to the use of a voltage multiplier (e.g., a voltage doubler or a voltage tripler) and avoids amplitude increases that trigger the voltage multiplier when possible. Accordingly, a preferred device monitors the present battery voltage and the current amplitudes from each site of the cardiac stimulation device and attempts duration increases when such increases avoid triggering the voltage multiplier, e.g., when the other site does not require the voltage multiplier.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
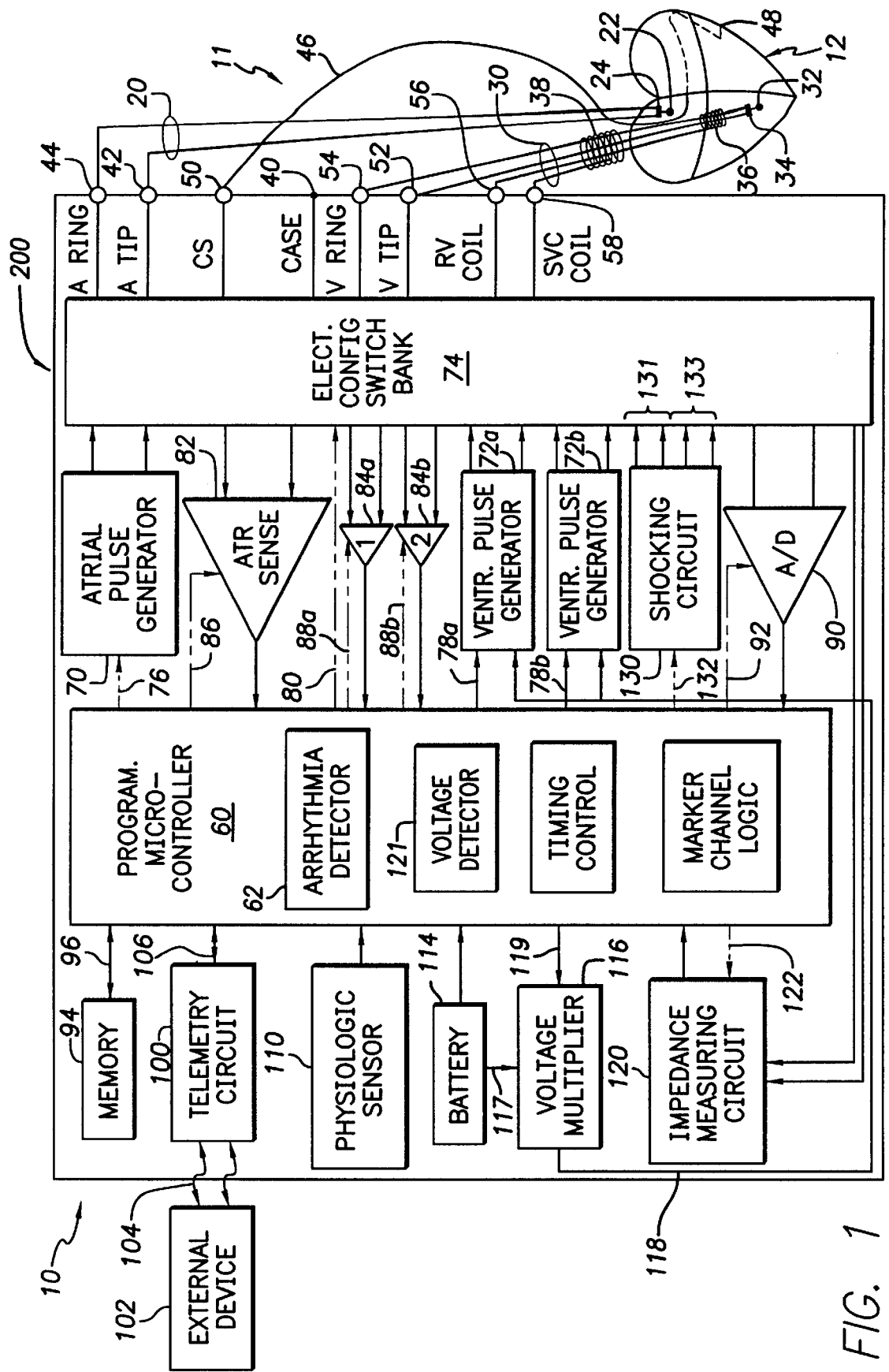
FIG. 1 shows a simplified functional block diagram of an implantable cardioverter/defibrillator (ICD) configured for stimulating multiple sites in a patient's heart, which represents one type of implantable cardiac stimulation device with which the present invention may be used.

In FIG. 1, a simplified block diagram is shown of an implantable cardiac stimulation system 200 including a dual-chamber implantable stimulation device 10 and a lead system 11. The system 200, as will be seen hereinafter, is capable of treating both fast and slow arrhythmias with stimulation therapy, including atrial and ventricular cardioversion, defibrillation, and pacing stimulation. While a combined pacer and defibrillator device is shown, this is for illustration purposes only, and one of skill in the art could readily eliminate or disable the defibrillator circuitry to provide a stimulation only device, eliminate or disable the pacing circuitry to provide a single or dual-chamber defibrillation device or add circuitry to provide a device capable of providing stimulation and/or defibrillation to three or four cardiac chambers without departing from the present invention.

To provide atrial chamber pacing stimulation and sensing, the implantable stimulation device 10 is shown in electrical communication with a patient's heart 12 by way of an implantable atrial lead 20 of lead system 11 having an atrial tip electrode 22 and an atrial ring electrode 24 which typically is implanted in the patient's atrial appendage.

The implantable stimulation device 10 is also shown in electrical communication with the patient's heart 12 by way of an implantable right ventricular lead 30 of lead system 11 having, in this embodiment, a right ventricular tip electrode 32 (positioned proximate to the right ventricular apex), a right ventricular ring electrode 34, a right ventricular (RV) defibrillation coil electrode 36, and a defibrillation coil electrode 38. Typically, the right ventricular lead 30 is transvenously inserted into the heart 12 so as to place the RV coil electrode 36 in the right ventricle, and the coil electrode 38 in the superior vena cava (SVC) or the right atrium. Accordingly, the right ventricular lead 30 is capable of receiving cardiac signals and delivering stimulation therapy in the form of pacing and shock therapy to the right ventricle and right atrium.

Further, in accordance with this preferred embodiment, the lead system preferably includes a coronary sinus (CS) lead 46 having an electrode 48. The CS lead 46 may be advanced through the SVC, into the right atrium, through the os or ostium of the coronary sinus, and into the coronary sinus for placing the electrode 48 proximate to the left ventricle. Alternatively, the lead 46 may be advanced into any of the left ventricular veins, such as the left cardiac vein in order to provide left ventricular pacing.

The housing 40 (shown schematically) for the implantable stimulation device 10 includes a connector (not shown) having an atrial tip terminal 42 and an atrial ring terminal 44, which are adapted for connection to the atrial tip electrode 22 and the atrial ring electrode 24, respectively. The housing 40 further includes a right ventricular tip terminal 52, a right ventricular ring terminal 54, a right ventricular shocking terminal 56, and an SVC shocking terminal 58, which are adapted for connection to the right ventricular tip electrode 32, the right ventricular ring electrode 34, the RV coil electrode 36, and the SVC coil electrode 38, respectively. The housing 40 still further includes a CS pin terminal 50 adapted for connection to the CS coil electrode 48 for stimulating the left ventricle of the patient's heart. The housing 40 (often referred to as the "enclosure", "can", "case" or "case electrode") encapsulates the circuitry of the implantable stimulation device 10 and is formed of electrically conductive material. It may be programmably selected to serve as a return defibrillation electrode, alone or in combination with one of the coil electrodes or as a return electrode for one or more of the tip electrodes 22, 32 or 48.

At the core of the implantable stimulation device 10 is a programmable microcontroller 60, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. Representative types of control circuitry that may be used with the invention include the microprocessor-based control system of U.S. Pat. No. 4,940,052 (Mann et al.) and the state-machines of U.S. Pat. Nos. 4,712,555 (Thornander et al.) and U.S. Pat. No. 4,944,298 (Sholder). For a more detailed description of the various timing intervals used within the stimulation device and their inter-relationship, see U.S. Pat. No. 4,788,980 (Mann et al.). The '052, '555, '298 and '980 patents are incorporated herein by reference.

As shown in FIG. 1, an atrial pulse generator 70 and ventricular pulse generators 72a and 72b generate pacing stimulation pulses for delivery by the atrial lead 20, the ventricular lead 30, and the CS lead 46, respectively, via a switch bank 74. The pulse generators, 70, 72a, and 72b are controlled by the microcontroller 60 via appropriate control signals, 76, 78a and 78b, respectively, to trigger or inhibit the stimulation pulses. The microcontroller 60 further includes timing circuitry that controls the timing of such stimulation pulses, e.g., pacing rate, atrio-ventricular (AV) delay) and the interventricular delay, as well as keeping track of the timing of any refractory periods, PVARP intervals, noise detection windows, evoked response windows, alert intervals, marker channel timing, etc., that are well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches as is known in the art.

An atrial sense amplifier 82 and ventricular sense amplifiers 84a and 84b are also coupled to the atrial and ventricular leads 20, 30 and 46, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82, 84a and 84b, preferably employs a low power, precision amplifier with programmable gain and/or automatic gain control, bandpass filtering, and a threshold detection circuit, known in the art, to selectively sense the cardiac signal of interest. The automatic gain control enables the implantable stimulation device 10 to deal effectively with sensing the low frequency, low amplitude signal characteristics of atrial and ventricular fibrillation.

The outputs of the atrial and ventricular sense amplifiers, 82, 84a and 84b, are connected to the microcontroller 60 which, in turn, inhibits the atrial and ventricular pulse generators, 70, 72a and 72b, respectively, in a demand fashion whenever cardiac activity is sensed in the respective chambers. The sense amplifiers, 82, 84a and 84b, in turn, receive control signals over signal lines, 86, 88a and 88b, from the microcontroller 60 for purposes of controlling the gain, threshold, polarization charge removal circuitry (not shown), and the timing of any blocking circuitry (not shown) coupled to the inputs of the sense amplifiers, 82, 84a and 84b, as is known in the art.

For arrhythmia detection, the device preferably includes an arrhythmia detector 62 which utilizes the atrial and ventricular sense amplifiers, 82, 84a and 84b, to sense cardiac signals to determine whether a rhythm is physiologic or pathologic. As used herein, "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (e.g., bradycardia, normal, low rate VT, high rate VT, and atrial and ventricular fibrillation rate zones) and various other characteristics (e.g., sudden onset, stability, physiologic sensors, and morphology, etc.) in order to determine the type of arrhythmia detected (e.g., bradycardia, tachycardia, and atrial or ventricular fibrillation), to employ a corresponding arrhythmia terminating therapy, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20, 30 and 46, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the implantable stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the implantable stimulation device 10 (as contained in the microcontroller 60 or memory 94) to be sent to the external device 102 through an established communication link 104.

In a preferred embodiment, the implantable stimulation device 10 may further include a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70, 72a and 72b, generate stimulation pulses. The type of sensor used is not critical to the present invention and is shown only for completeness.

The stimulation device additionally includes a battery 114 which provides operating power to all of the circuits shown in FIG. 1. For the exemplary implantable stimulation device 10, which employs shocking therapy, the battery 114 must be capable of operating at low current drains for long periods of time (preferably less than 10 $\mu$A) and then be capable of providing high-current pulses (for capacitor charging) when the patient requires a shock pulse (preferably, in excess of 2 amps at voltages above 2 volts, for periods of 10 seconds or more). The battery 114 preferably has a predictable discharge characteristic so that elective replacement time can be detected. Accordingly, the implantable stimulation device 10 preferably employs lithium/silver vanadium oxide batteries, as is true for most (if not all) current devices.

Furthermore, a voltage multiplier 116, powered by the battery 114 via power line 117, may be used to provide the stimulation voltage needed by the ventricular pulse generators 72a and 72b to stimulate the patient's heart. Preferably, a single voltage multiplier 116 (e.g., a voltage doubler or tripler) is used to power both the ventricular pulse generators 72a and 72b via line 118. Accordingly, if either pulse generator requires a voltage in excess of a voltage multiplier threshold voltage $V_M$ (i.e., the present battery voltage $V_B$ minus a factor to accommodate the operation of the voltage multiplier; generally this voltage approximates the battery voltage), the voltage multiplier 116 may be triggered via line 119 for powering both pulse generators 72a and 72b. Due to potential power losses in the voltage multiplier 116, triggering the voltage multiplier 116 is preferably avoided, when possible. The battery voltage is periodically monitored by a voltage detector 121. As discussed further below, the microcontroller 60 preferably determines whether to trigger the voltage multiplier 116 as a function of the present battery voltage and the voltage (or current) amplitude signal presently demanded by each of the pulse generators in order to achieve capture. The use of multiple voltage multipliers is considered to be within the scope of the present invention and will enable the use of a simpler control algorithm at the expense of the additional hardware, package volume and potential power dissipation. However, specific aspects of the present invention are adapted to enable the use of a single voltage multiplier and thus minimize hardware, package volume and power dissipation.

The implantable stimulation device 10 further includes a magnet detection circuitry (not shown), coupled to the microcontroller 60. It is the purpose of the magnet detection circuitry to detect when a magnet is placed over the implantable stimulation device 10, which magnet may be used by a clinician to perform various test functions of the implantable stimulation device 10, such as defibrillation threshold tests, and/or to signal the microcontroller 60 that the external programmer 102 is in place to receive or transmit data to the microcontroller 60 through the telemetry circuit 100.

As previously discussed, the stimulation threshold energy level can be significantly different between the right and left sides of the patient's heart. Accordingly, embodiments of the present invention provide independent control of the voltage (or current) and pulse duration components of stimulation pulses for each side of the patient's heart. Furthermore, a delay between pacing pulses provided to the right and left sides of the patient's heart is preferably programmable to alternatively enable optimal hemodynamics or treatment of the patient's heart. Such programmable data may be provided via remotely entered data from the external device 102 that communicates with the telemetry circuit 100. Alternatively, as discussed further below, the time delay may be automatically configurable dependent upon measured propagation delays.

In order to obtain independent stimulation energy control between the right and left sides of the patient's heart, individual ventricular pulses generators 72a and 72b are provided under individual control from the microcontroller 60 via control lines 78a and 78b. The initial energy threshold levels may be remotely programmable as described above. However, in a preferred embodiment, the initial right and left threshold energy levels are determined according to calculated strength-duration curves. A first alternative technique will now be described.

An equation for approximating the relationship between amplitude and duration for stimulating body, e.g., cardiac tissue, was defined in 1909 by Lapicque as a strength-duration curve. The Lapicque equation is:

$$I = I_R * (1 + d_c/d)$$

where $I_R$ represents the lead current at the rheobase, i.e., the lowest current pulse (independent of duration) that can stimulate the body tissue and $d_c$ represents the chronaxie time duration, i.e., a duration at which stimulation requires twice the rheobase current value for capture.

This relationship is readily apparent by setting d equal to $d_c$ which results in:

$$I = 2 * I_R.$$

This equation can be adjusted to calculate stimulation voltage by multiplying each side by the lead impedance, resulting in:

$$V = V_R * (1 + d_c/d)$$

Where $V_R$ is the rheobase voltage.

The chronaxie and rheobase may be calculated using the present device. As described below, this calculation may be accomplished using only two sets of measurements.

The amount of charge Q that is needed to stimulate the cardiac tissue can be expressed as:

$$Q = I * d$$

where I is current and d is the pulse duration.

As previously discussed, the stimulation current can be expressed as:

$$I = I_R * (1 + d_c/d)$$

It is thus known that:

$$Q = I_R * (1 + d_c/d) * d$$
$$= (I_R * d) + (I_R * d_c)$$
$$= I_R * (d + d_c)$$

If a fixed pulse duration is selected, and a stimulation pulse is generated, e.g., from ventricular pulse generator 72a, its corresponding sense amplifier, e.g., ventricular sense amplifier 84a, will attempt to detect an evoked response. (Alternatively, the data acquisition system 90 may be used to detect an evoked response.) An evoked response will typically occur within a window of 15 to 50 milliseconds subsequent to the delivery of the stimulation pulse. Accordingly, the ventricular sense amplifier 84a is preferably blanked via signal line 88a for the time preceding this detection window. If an evoked response does not occur, the amplitude of the stimulation pulse is increased, e.g., by a relatively small (fine) quantity, and the test is repeated. When an evoked response is detected, a point on the strength-duration curve has been found.

If this test process is repeated twice, one can arithmetically derive the rheobase and the chronaxie. For example, when the tests are repeated for exemplary values of d equal to 1.0 and 2.0 milliseconds (one of ordinary skill in the art can adapt these calculations for other test values, see for example, Equations 2 and 3 of U.S. Pat. No. 5,447,525), the following two equations result, respectively:

$$Q_{(1)} = I_R * (1 + d_c) = I_R + (I_R * d_c)$$

$$Q_{(2)} = I_R * (2 + d_c) = (2 * I_R) + (I_R * d_c)$$

Accordingly:

$$Q_{(2)} - Q_{(1)} = I_R$$

i.e., the rheobase current is the difference between the two charges (where Q is in millicoulombs and $I_R$ is in amperes). If the equation is multiplied by resistance R and the charges are adjusted for their 2.0 millisecond and 1.0 millisecond durations, the rheobase voltage may be determined by the equation:

$$V_R = (2 * V_{(2)}) - V_{(1)}$$

i.e., the rheobase voltage can be calculated from the two measured voltages at which capture occurred.

Further substituting the solved rheobase voltage value $((2 * V_{(2)}) - V_{(1)})$ in the Lapicque voltage equation at 1.0 milliseconds, it is determined that:

$$V = V_R * (1 + d_c/d)$$

$$V_{(1)} = ((2 * V_{(2)}) - V_{(1)}) * (1 + (d_c/1))$$

$$V_{(1)} = ((2 * V_{(2)}) - V_{(1)}) * (1 + d_c)$$

And thus, the chronaxie value (in milliseconds) may be determined by the following equation with measurements made at duration values of 1.0 and 2.0 milliseconds:

$$d_c = (V_{(1)}/((2 * V_{(2)}) - V_{(1)})) - 1$$

In a second alternative technique, the rheobase can be approximated by observing that typically the Lapicque curve is essentially flat at or beyond the 2.0 millisecond point. Thus, if a voltage capture level is obtained at or beyond that point, it will approximate the rheobase. Next, using twice the measured rheobase value for the pulse amplitude, the pulse duration can be incremented from a starting point, e.g., 0.5 milliseconds, until an evoked response occurs within the detection window. This point of capture is then identified as the chronaxie value.

These techniques are preferably used to independently determine the rheobase and chronaxie for each side of the patient's heart using the right ventricular pulse generator 72a and right ventricular sense amplifier 84a for the right side calculation and the left ventricular pulse generator 72b and left ventricular sense amplifier 84b for the left side calculation. The sense amplifiers may be able to sense far field signals propagating from the opposing heart side. Accordingly, to avoid misdetecting a far field signal as a locally evoked response, it is preferable that the described rheobase and chronaxie calculations only occur on one side of the heart at a time, i.e., the stimulation pulses are temporarily suppressed on the opposing side.

By definition, the strength-duration curve defines point pairs (voltage, duration) at which capture can be achieved. It has further been determined that the point with an amplitude of twice the rheobase and a duration that is equal to the chronaxie is the point on the strength-duration curve that will minimize power consumption and thus maximize battery life. This point is sometimes referred to as the chronaxie point. However, due to physiological and measurement variations, one or more parameters should be increased to achieve a safety margin above this optimal energy level. Furthermore, various physiological factors may require increases in this safety-factored energy level as well as periodically enabling the energy level to be decreased. These concepts are generally used in the previously referenced device, the Affinity® DR, Model 5330 L/R Dual-Chamber Pulse Generator, manufactured by the assignee of the present invention as well as the previously reference pending U.S. patent application Ser. No. 09/483,908, both of which have been incorporated herein by reference.

Figure 2A:
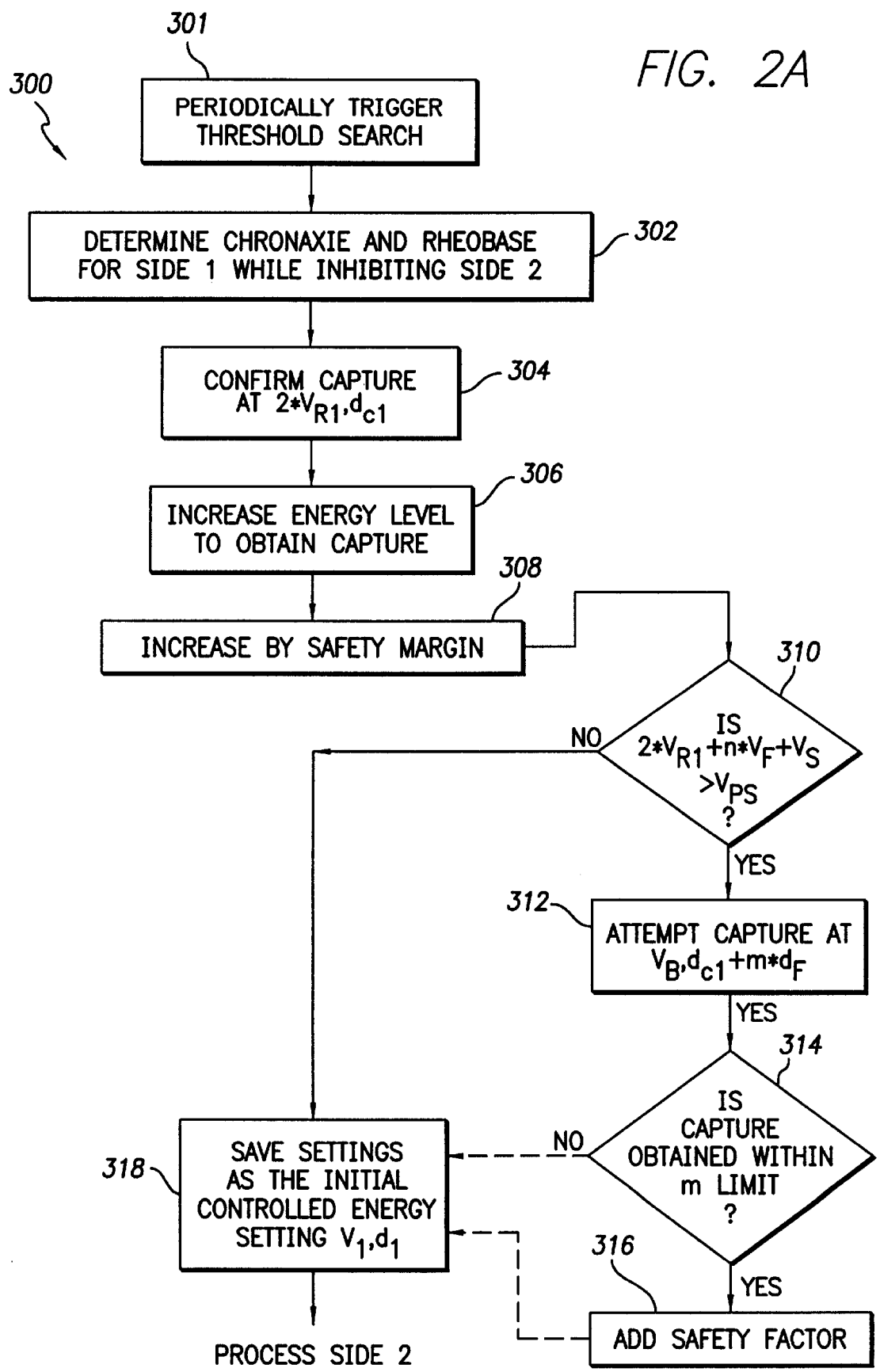
FIGS. 2A and 2B show an exemplary flow chart of a threshold search routine for independently determining an initial energy threshold level plus a safety margin for each side of the patient's heart.
Figure 2B:
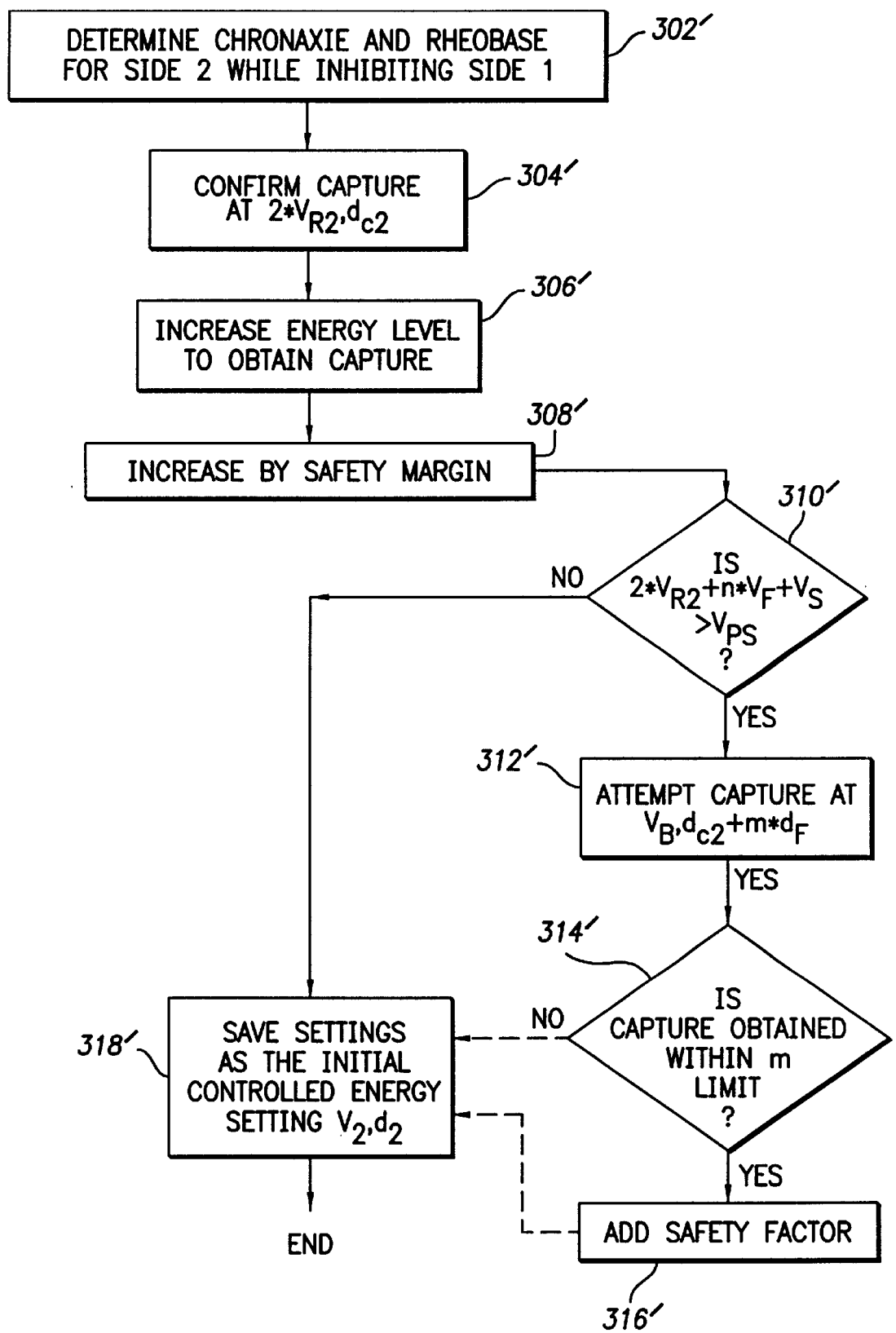

FIGS. 2A and 2B show simplified exemplary flow charts of the aforementioned process for a threshold search routine 300 for determining the initial energy threshold levels plus safety margins. Periodically, e.g., every 6 to 24 hours as shown in step 301 or as required by the loss-of-capture algorithm described below, the threshold search routine 300 determines in step 302 the chronaxie ($d_{c1}$) and rheobase ($V_{R1}$) for one side (i.e., side 1) of the heart. During this determination, stimulation pulses are inhibited on the opposing side (i.e., side 2) of the heart in order to avoid mistaking a far field signal for an evoked response. Step 302 may proceed according to one of the aforedescribed techniques or equivalent. While this technique is only specifically described in reference to FIG. 2A for one side (side 1, e.g., the right side) of the patient's heart, it is preferred that this procedure additionally and alternately be used for each side of the heart, see FIG. 2B which shows the procedure for the other side (side 2, e.g., the left side) of the patient's heart. As previously discussed, it is preferred that these procedures alternate to avoid erroneously detecting a far field signal for an evoked response.

In step 304, it is confirmed that the determined chronaxie point ($2*V_{R1}$, $d_{c1}$) satisfactorily captures the patient's heart and in step 306 the energy level is increased if necessary to obtain capture. It is noteworthy that the first alternative technique for determining the strength-duration curve calculates the location of the chronaxie point and, as such, the determination in step 304 is the first time that this confirmation is made. However, the second alternative technique for determining the strength-duration curve selects an approximate chronaxie point based upon an approximate rheobase point. Nevertheless, the determination of step 304 would occur at this approximate, but previously measured, point. Accordingly, if the second alternative technique is used, steps 304 and 306 may be skipped.

Typically automatic capture systems use a stimulation energy curve where the pulse duration is predetermined and the stimulation voltage is increased by a relatively small (i.e., fine) voltage factor $V_F$ above the amplitude level at the chronaxie point of twice the rheobase ($2*V_{R1}$) until capture is achieved at a capture energy level. Accordingly, capture is confirmed at a voltage value of $(2*V_{R1})+(n*V_F)$, and a duration point of $d_{c1}$, where n corresponds to the number of fine $V_F$ steps, e.g., steps of 0.1 volts, that are taken to regain capture. This voltage, duration point pair may also be referenced as:

$$(2*V_{R1})+(n*V_F), d_{c1}$$

Next, the voltage level is preferably increased by a safety margin $V_S$ in step 308 to ensure that the system will be tolerant of variations in the strength-duration curve or the measurement circuitry. The safety margin may alternatively be preprogrammed by the microcontroller 60 or may be remotely programmable via the external device 102. The determined controlled energy level is subsequently saved in step 318. It is preferable to avoid triggering the voltage multiplier in order to conserve power. Accordingly, it is first determined in step 310 if the proposed voltage component, $(2*V_{R1})+(n*V_F)+V_S$, exceeds a voltage which corresponds to the present battery voltage as measured by the voltage detector 121 adjusted by a factor related to the operation of the voltage multiplier (the significance of voltage $V_{PS}$ in the preferred dual site environment is described below). If the proposed voltage component is below this value, the proposed voltage component becomes the initial voltage component in step 318. The stimulation point used (expressed as amplitude, duration) is:

$$(2*V_{R1})+(n*V_F)+V_S, d_{c1}$$

Additionally, this determination is moot if the other side of the heart already requires triggering of the voltage multiplier. Accordingly, the determination in step 310 is preferably done relative to a voltage value $V_{PS}$ which is the highest multiple of the voltage multiplier threshold voltage $V_M$ required by either the right or the left side of the heart.

If it is determined that the opposing heart side does not require the voltage multiplier, triggering the voltage multiplier is postponed in step 312 where the amplitude portion of the stimulation pulse (i.e., the voltage component) is set to the present battery voltage $V_B$ and the duration component is increased from the chronaxie duration value $d_{c1}$. Thus, capture is attempted at:

$$V_B, d_{c1}+(m*d_F)$$

where $d_F$ is a relatively small (fine) duration increment (e.g., 0.05 milliseconds) and m is the number of steps used to regain capture. If capture is obtained in step 314, the pulse duration is increased by a pulse duration safety factor $d_S$ in step 316, resulting in an initial stimulation point of:

$$V_B, d_{c1}+(m*d_F)+d_S$$

The pulse duration safety factor $d_S$ may be preprogrammed in the microcontroller 60 or may be programmable from the external device 102.

Alternatively, the value determined in step 310 becomes the initial stimulation point and the voltage multiplier is triggered as needed. This stimulation point may be expressed as:

$$(2*V_{R1})+(n*V_F)+V_S, d_{c1}$$

Figure 3:
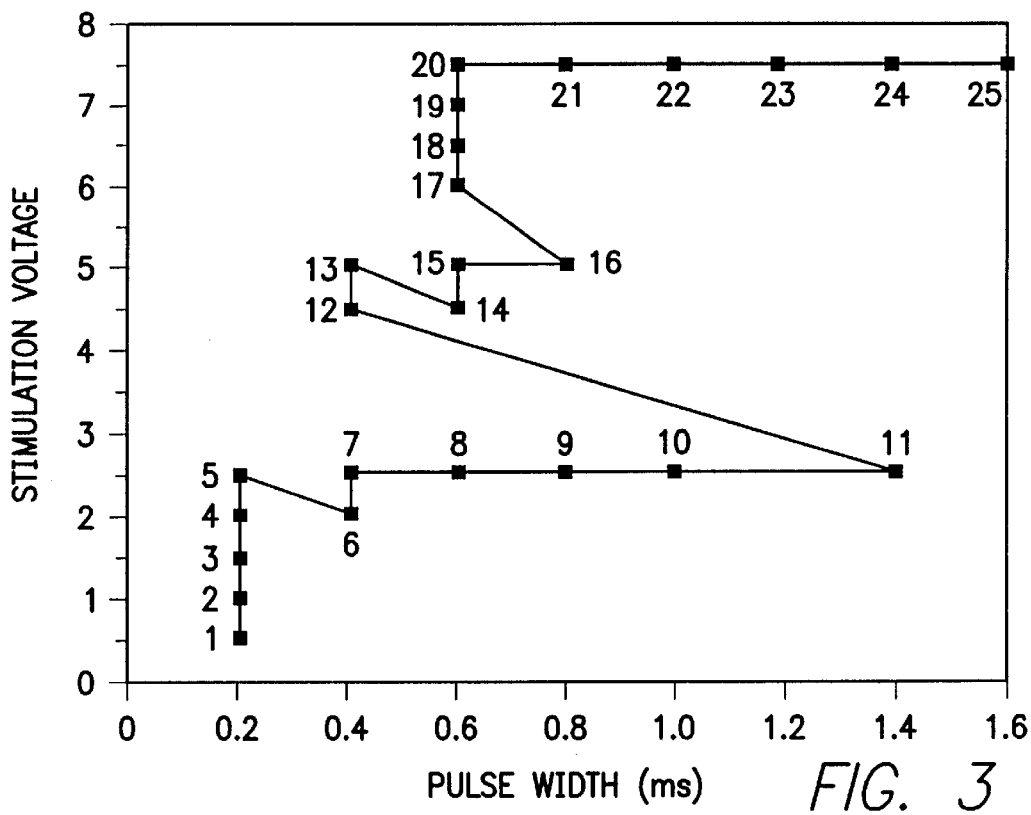
FIG. 3 is a copy of FIG. 7 from U.S. Pat. No. 5,697,956 to Bornzin which shows an exemplary stimulation energy curve suitable for use with the present invention.

In an alternative implementation, the chronaxie determined energy level is increased in step 306 by a function of voltage and duration, e.g., using the curve described in FIG. 7 of Bornzin which is included herein as FIG. 3. Accordingly, the stimulation point at capture may be represented by:

$$(2*V_{R1})+(n*V_F), d_{c1}+(n*d_F)$$

Accordingly, in step 308 where the energy level is increased to achieve a safety margin, this may be accomplished by simply increasing the value of n by a safety factor $n_S$ that may be preprogrammed in the microcontroller 60 or may be programmable from the external device 102. Thus, the stimulation point at capture may be represented by:

$$(2*V_{R1})+((n+n_S)*V_F), d_{c1}+((n+n_S)*d_F)$$

By using the Bornzin curve (now of FIG. 3), the ability to avoid triggering the voltage multiplier is built into the curve, i.e., the Bornzin curve has been formed to include the effect of the voltage multiplier. For additional details of the forming of this curve, see U.S. Pat. No. 5,697,956. It should be noted that the Bornzin curve is not uniformly monotonic in voltage. See, for example, point 6 where the pulse duration is increased to avoid increasing the pulse amplitude above the voltage threshold of the voltage multiplier. At point 6, the pulse amplitude is decreased to minimize the energy increase caused by the pulse amplitude increase and thus limits the energy increase between points 5 and 6. However, the Bornzin curve does not take into account the current dual site environment.

The stimulation energy curve is preferably updated periodically. First, the Bornzin curve is preferably updated to compensate for altering the voltage multiplier threshold voltage $V_M$ as the battery voltage $V_B$ is depleted. Next, curve plateau levels, corresponding to the voltage multiplier that is already used by the opposing side of the heart, are eliminated.

Figure 4:
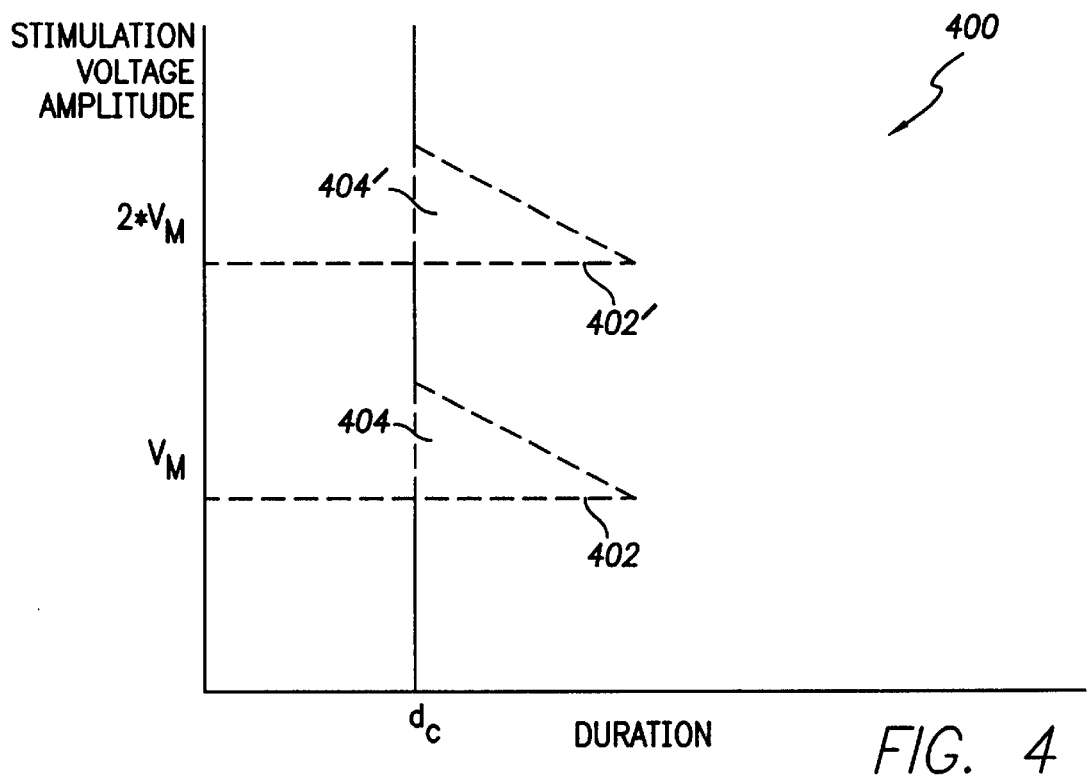
FIG. 4 shows a next exemplary stimulation energy curve suitable for use with the present invention.

A simplified stimulation energy (voltage, duration) curve 400 is shown in FIG. 4 to illustrate these effects. In FIG. 4, the voltage component is allowed to increase with a fixed duration (preferably at the chronaxie) until the voltage multiplier threshold voltage $V_M$ is reached. At that point, only the duration component of the stimulation pulse is permitted to increase. Eventually, if capture cannot be achieved, the curve returns to its initial duration component value and the voltage component again increases. This transition will require use of the voltage multiplier. However, if the opposite side of the heart has already required the voltage multiplier, the jog 402 in the curve to accommodate the voltage multiplier is unnecessary. Accordingly, jog 402 will be eliminated and the curve will return to its upward transition 404. Thus, the curve is dynamically reformatted in response to changes in battery voltage and demands of the opposite side of the heart. Similar reformatting (see 402' and 404') may occur in response to reaching the voltage level used for triggering a voltage tripler. It is believed that, while not essential, the use of a Bornzin type stimulation energy curve simplifies the practice of the present invention. Furthermore, an improved stimulation energy curve is described in U.S. Pat. No. 6,456,879, filed Oct. 5, 2000, entitled "Method and Device For Optimally Altering Stimulation Energy to Maintain Capture of Cardiac Tissue," and copending U.S. patent application Ser. No. 09/685,331, filed Oct. 5, 2000, entitled "Method and Device For Optimally Altering Stimulation Energy to Maintain Capture of Cardiac Tissue," which are both based on commonly-assigned U.S. Provisional Application No. 60/204,317, filed May 15, 2000, entitled "Method and Device For Optimally Altering Stimulation Energy to Maintain Capture of Cardiac Tissue," the teachings of which are incorporated herein by reference in their entirety. The stimulation energy curve in such application is additionally optimized for variations in the chronaxie as well as the rheobase and thus is less susceptible to strength-duration curve variations. The use of such a stimulation energy curve is equally applicable to the present invention.

Figure 5:
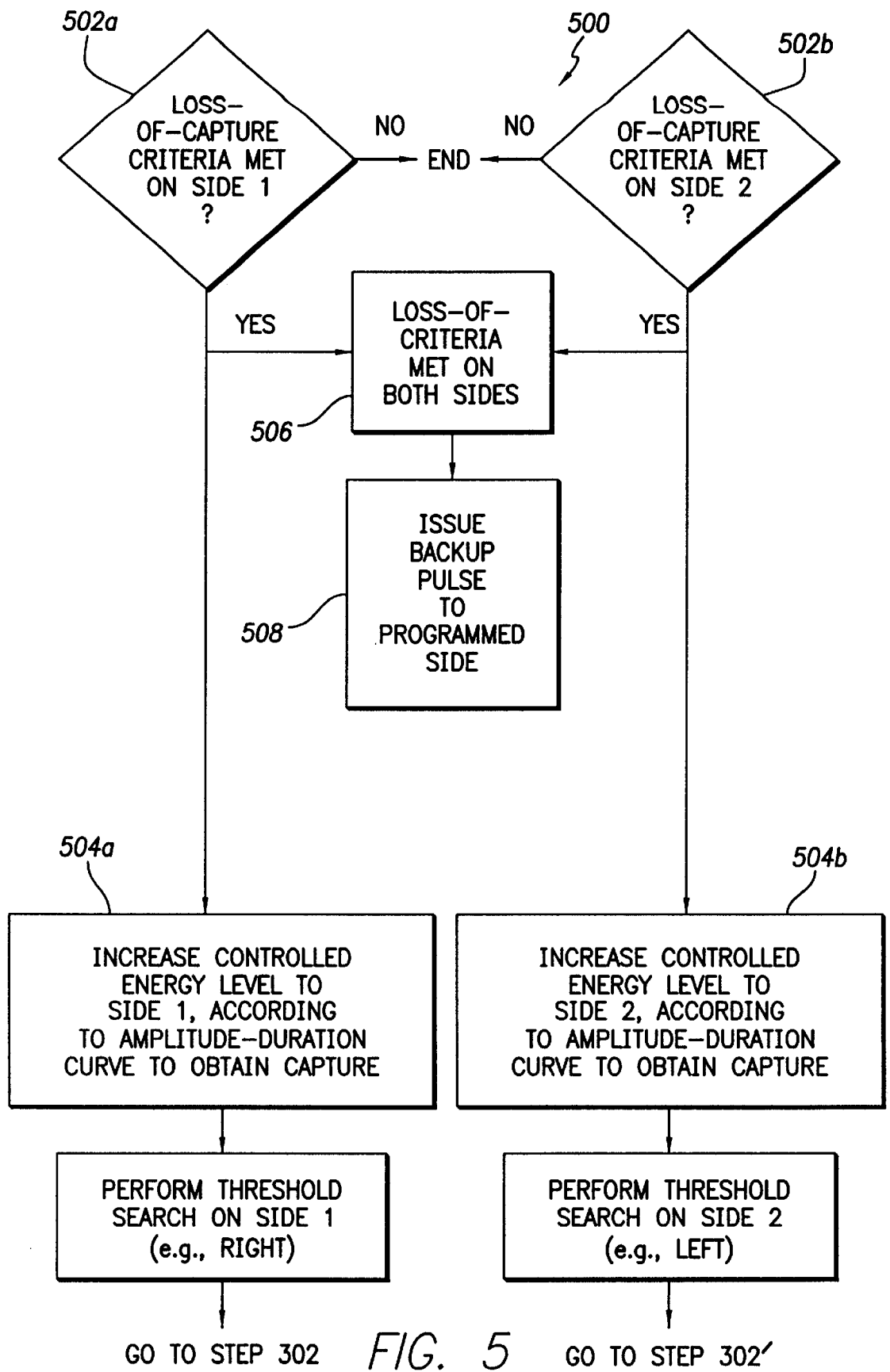
FIG. 5 shows an exemplary flow chart of a capture verification routine for independently maintaining capture of each side of the patient's heart.

FIG. 5 shows a simplified flow chart 500 for maintaining capture of both sides of the patient's heart. Initially in steps 502a and 502b, it is determined whether a loss-of-capture criteria has been met. For instance, in an exemplary device, the Affinity® DR, Model 5330 L/R Dual-Chamber Pulse Generator, manufactured by the assignee of the present invention, the absence of two consecutive evoked responses defines a loss-of-capture criteria while the aforementioned U.S. patent application Ser. No. 09/483,908 defines a loss-of-capture criteria as X out of the last Y beats, where Y is greater than 2 and X is less than Y. Once a loss-of-capture criteria is met, the controlled energy level is increased in steps 504a and 504b. Preferably, the controlled energy level is increased (preferably by a relatively large, i.e., coarse, value $V_C$ to rapidly regain capture) according to the aforementioned criteria of U.S. Pat. No. 5,697,956 or the aforementioned copending application to Mandell, each of which additionally provides the benefit of avoiding use of the voltage multiplier 116 when possible. Alternatively, the voltage component alone may be increased by a coarse value $V_C$ to regain capture. Thus, capture will be regained for side 1 in block 504a at a value of $V_1+n*V_C$, $d_1$. Similarly, capture will be regained for side 2 in block 504b at a value of $V_2+n*V_C$, $d_2$. Once capture has been regained, the associated threshold search routine 302 or 302' is preferably triggered to redetermine the threshold level for the appropriate side of the patient's heart. Preferably, only the side that has been recaptured starts a new threshold search.

As opposed to single site automatic capture algorithm, as found in the aforementioned Affinity® DR, Model 5330 L/R Dual-Chamber Pulse Generator, a loss-of-capture is not considered to be as serious since the opposite side, e.g., chamber, of the heart can be considered to be providing a source for a delayed stimulation pulse (somewhat analogous to a backup pulse), albeit delayed resulting from the wave propagation delay between sides. Accordingly, a backup pulse, typically at a 4.5 volt level, need only be provided if both sides fail to capture, as detected in step 506. Accordingly, in such an event a backup pulse is delivered to one or both chambers in step 508. Preferably, this determination is programmable from the external device 102.

Preferably, the right and left ventricular pulse generators 72a and 72b can deliver stimulation pulses with an adjustable interventricular delay as timed by the timing control circuit 124 in the microcontroller 60. In a healthy heart, it is hemodynamically optimal to simultaneously pace the left and right ventricles of the patient's heart. Accordingly in a first embodiment, the right and left stimulation pulse are delivered simultaneously but with different, alterable energy levels. However, in a CHF patient or the like, this may not be the optimal treatment. Accordingly, in a preferred embodiment, one side of the heart, e.g., the right side, is paced independent of the other side and the opposing sense amplifier monitors for a far field signal. If the far field signal occurs within 100 milliseconds, this may be considered to be a normal condition and simultaneous stimulation may continue. However, if the far field signal occurs at a time period greater than 100 milliseconds, e.g., 160 milliseconds, it may be preferable to set the interventricular delay, i.e., the time delay between right and left stimulation pulses, to a percentage of the measured delay, e.g., 50%. Thus, in this example, the interventricular delay would be set to 80 milliseconds. Alternatively, it may be desirable to stimulate the left ventricle in advance of the right ventricle, i.e., to set the interventricular delay to a negative value, to attempt to overcome the disease process. This delay, positive or negative, may be adjusted to optimize the heart's output as sensed by a hemodynamic sensor.

Accordingly, what has been shown is an improved criteria for performing an automatic capture/threshold procedure in an implantable cardiac stimulation device. While the invention has been described by means of specific embodiments and applications thereof, it is understood that numerous modifications and variations could be made thereto by those skilled in the art without departing from the spirit and scope of the invention. Specifically, while the invention has been specifically described in reference to embodiments that individually stimulate the left and right ventricles, embodiments that individually stimulate the left and right atrium or two or more other individual sites in the heart, e.g., right atrium and left ventricle, are also considered to be within the scope of the present invention. It is therefore to be understood that within the scope of the claims, the invention may be practiced otherwise than as specifically described herein.

What is claimed is:

1. A method for pacing a patient's heart using a battery powered implantable stimulation device connected to at least two electrodes implanted in a patient's heart wherein a first electrode is positioned to stimulate a chamber in the right side of the patient's heart and the second electrode is positioned to stimulate a corresponding chamber in the left side of the patient's heart, the method comprising the steps of:

periodically stimulating the right side of the patient's heart with a first stimulation pulse having a first controlled energy level wherein the first controlled energy level is defined by a set of characteristics including a first amplitude component and a first duration component;

detecting the presence or absence of an evoked response generated by the right side of the patient's heart in response to the first stimulation pulse during a first detection window;

increasing the first controlled energy level in response to a loss-of-capture criteria related to the absence of an evoked response from the right side of the patient's heart;

periodically stimulating the left side of the patient's heart with a second stimulation pulse having a second controlled energy level wherein the second controlled energy level is defined by a set of characteristics including a second amplitude component and a second duration component;

detecting the presence or absence of an evoked response generated by the left side of the patient's heart in response to the second stimulation pulse during a second detection window;

increasing the second controlled energy level in response to a loss-of-capture criteria related to the absence of an evoked response from the left side of the patient's heart; wherein the step of periodically stimulating the left side of the patient's heart additionally comprises the step of setting a time between stimulating the left and right sides of the heart to a determined delay period from the stimulation of the right side of the patient's heart by the first stimulation pulse;

periodically measuring the present output voltage of the battery which powers the implantable stimulation device; and wherein the steps of increasing the first and second controlled energy levels are dependent upon the first and second amplitude components and the present battery output voltage.

2. The method of claim 1 wherein:

the step of increasing the first controlled energy level comprises the steps of:

determining a proposed increased first amplitude component for generating a first stimulation pulse which will result in the presence of an evoked response from the right side of the patient's heart;

making a first determination if the proposed increased first amplitude component will exceed a voltage corresponding to the present battery output voltage; and varying the first amplitude component dependent upon the second amplitude component and the first determination; and the step of increasing the second controlled energy level comprises the steps of:

determining a proposed increased second amplitude component for generating a second stimulation pulse which will result in the presence of an evoked response from the left side of the patient's heart;

making a second determination if the proposed increased second amplitude component will exceed the voltage corresponding to the present battery output voltage; and varying the second amplitude component dependent upon the first amplitude component and the second determination.

3. The method of claim 1 further comprising the step of setting the delay period to essentially 0.0 seconds.

4. The method of claim 1 further comprising the step of setting the delay period to cause the right side of the patient's heart to be stimulated before the left side of the patient's heart.

5. The method of claim 1 further comprising the step of setting the delay period to cause the left side of the patient's heart to be stimulated before the right side of the patient's heart.

6. The method of claim 1 further comprising the steps of:

periodically determining the chronaxie and rheobase corresponding to a strength-duration curve for the chamber on the right side of the patent's heart;

setting the first controlled energy level to an initial first controlled energy level related to the strength-duration curve for the right side of the patient's heart;

periodically determining the chronaxie and rheobase corresponding to a strength-duration curve for the chamber on the left side of the patient's heart; and setting the second controlled energy level to an initial second controlled energy level related to the strength-duration curve for the left side of the patent's heart.

7. The method of claim 6 further comprising the steps of:

setting the initial first controlled energy level to an amplitude value based on the amplitude value of the rheobase and a duration value of the chronaxie for the determined values corresponding to the chamber on the right side of the patient's heart; and setting the initial second controlled energy level to a value based on the amplitude value of the rheobase and a duration value of the chronaxie for the determined values corresponding to the chamber on the left side of the patient's heart.

8. The method of claim 7 wherein:

the setting the initial first controlled energy level step comprises setting the initial first controlled energy level to an amplitude value corresponding to twice the rheobase and a duration value of the chronaxie for the determined values corresponding to the chamber on the right side of the patient's heart; and the setting the initial second controlled energy level step comprises setting the initial second controlled energy level to an amplitude value corresponding to twice the rheobase and a duration value of the chronaxie for the determined values corresponding to the chamber on the left side of the patient's heart.

9. The method of claims 7 wherein the steps of setting the initial first and second controlled energy levels are functions of a safety margin value.

10. The method of claim 1 further comprising the steps of:

periodically determining the chronaxie and rheobase corresponding to the strength-duration curve for the chamber on the right side of the patient's heart;

periodically determining the chronaxie and rheobase corresponding to a strength-duration curve for the chamber on the left side of the patient's heart; and causing the periodically determining steps to occur at different times to avoid interactions between the two determinations.

11. The method of claim 1 wherein in response to detecting the absence of an evoked response on the right side of the patient's heart and the left side of the patient's heart, further including the step of delivering a backup pulse after a backup delay following delivery of the first of two stimulation pulses.

12. The method of claim 11 further comprising the step of delivering the backup pulse at an elevated energy level.

13. The method of claim 11 further comprising the step of delivering the backup pulse only to the right side of the patient's heart.

14. The method of claim 11 further comprising the step of delivering the backup pulse only to the left side of the patient's heart.

15. A method for pacing a patient's heart using an implantable stimulation device connected to at least two electrodes implanted in a patient's heart wherein a first electrode is positioned to stimulate the right ventricle of the patient's heart and the second electrode is positioned to stimulate the left ventricle of the patient's heart, the method comprising the steps of:

periodically stimulating the right ventricle of the patient's heart with a first stimulation pulse having a first controlled energy level wherein the first controlled energy level is defined by a set of characteristics including a first amplitude component and a first duration component;

detecting the presence or absence of an evoked response generated by the right ventricle of the patient's heart in response to the first stimulation pulse during a first detection window;

increasing the first controlled energy level in response to a loss-of-capture criteria related to the absence of an evoked response from the right ventricle of the patient's heart;

periodically stimulating the left ventricle of the patient's heart with a second stimulation pulse having a second controlled energy level wherein the second controlled energy level is defined by a set of characteristics including a second amplitude component and a second duration component;

detecting the presence or absence of an evoked response generated by the left ventricle of the patient's heart in response to the second stimulation pulse during a second detection window;

increasing the second controlled energy level in response to a loss-of-capture criteria related to the absence of an evoked response from the left ventricle of the patient's heart; wherein the step of periodically stimulating the left ventricle of the patient's heart additionally comprises the step of setting a time between stimulating the left and right ventricles of the patient's heart to a determined delay period from the stimulation of the right ventricle of the patient's heart by the first stimulation pulse; and periodically measuring the present output voltage of a battery which powers the implantable stimulation device; and wherein the steps of increasing the first and second controlled energy levels are dependent upon the first and second amplitude components and the present battery output voltage.

16. A method for pacing a patient's heart using an implantable stimulation device connected to at least two electrodes implanted in a patient's heart wherein a first electrode is positioned in the right ventricular apex to stimulate the right ventricle of the patient's heart and the second electrode is positioned in the coronary sinus to stimulate the left ventricle of the patient's heart, the method comprising the steps of:

periodically stimulating the right ventricle of the patient's heart with a first stimulation pulse having a first controlled energy level wherein the first controlled energy level is defined by a set of characteristics including a first amplitude component and a first duration component;

detecting the presence or absence of an evoked response generated by the right ventricle of the patient's heart in response to the first stimulation pulse during a first detection window;

increasing the first controlled energy level in response to a loss-of-capture criteria related to the absence of an evoked response from the right ventricle of the patient's heart;

periodically stimulating the left ventricle of the patient's heart with a second stimulation pulse having a second controlled energy level wherein the second controlled energy level is defined by a set of characteristics including a second amplitude component and a second duration component;

detecting the presence or absence of an evoked response generated by the left ventricle of the patient's heart in response to the second stimulation pulse during a second detection window;

increasing the second controlled energy level in response to a loss-of-capture criteria related to the absence of an evoked response from the left ventricle of the patient's heart; wherein the step of periodically stimulating the left ventricle of the patient's heart additionally comprises the step of setting a time between stimulating the left and right ventricle of the patient's heart to a determined delay period from the stimulation of the right ventricle of the patient's heart by the first stimulation pulse; and periodically measuring the present output voltage of a battery which powers the implantable stimulation device; and wherein the steps of increasing the first and second controlled energy levels are dependent upon the first and second amplitude components and the present battery output voltage.

17. An implantable cardiac stimulation device configured for stimulating a patient's heart through at least two electrodes wherein a first electrode is positioned to stimulate a chamber in the right side of the patient's heart and the second electrode is positioned to stimulate a corresponding chamber in the left side of the patient's heart, the stimulation device comprising:

a first pulse generator configured for electrical coupling to the first electrode and configured to generate first stimulation pulses at a first controlled energy level to thereby stimulate the right side of the patient's heart, wherein the first controlled energy level is defined by a set of characteristics including an amplitude component and a duration component;

a first detection circuit configured for electrical coupling to the first electrode and configured to receive cardiac signals for determining the presence or absence of an evoked response to each of the first stimulation pulses;

a second pulse generator configured for electrical coupling to the second electrode and configured to generate second stimulation pulses at a second controlled energy level to thereby stimulate the left side of the patient's heart, wherein the second controlled energy level is defined by a set of characteristics including an amplitude component and a duration component;

a second detection circuit configured for electrical coupling to the second electrode and configured to receive cardiac signals for determining the presence or absence of an evoked response to each of the second stimulation pulses;

a controller coupled to the first and second pulse generators and the first and second detection circuits for adaptively determining the first controlled energy level in response to the signals detected by the first detection circuit and for adaptively determining the second controlled energy level in response to signals detected by the second detection circuit;

a battery for providing power to the first and second pulse generators that generate the first and second stimulation pulses; and a voltage detector for detecting the present voltage level of the battery; and wherein the controller modifies the amplitude components of the first and second controlled energy levels dependent upon the present battery voltage level and the present first and second amplitude components.

18. The cardiac stimulation device of claim 17 wherein the controller periodically determines the chronaxie and rheobase corresponding to a strength-duration curve for the chamber on the right side of the patient's heart and determines an initial first controlled energy level accordingly.

19. The cardiac stimulation device of claim 18 wherein the controller periodically determines the chronaxie and rheobase corresponding to a strength-duration curve for the chamber on the left side of the patient's heart and determines an initial second controlled energy level accordingly.

20. The implantable cardiac stimulation device of claim 19 wherein the initial first and second controlled energy levels are selected to achieve a safety margin from the respective determined strength-duration curves, and wherein the controller determines the initial first and second controlled energy levels based upon a specified safety margin value.

21. The cardiac stimulation device of claim 17 wherein the controller periodically determines the chronaxie and rheobase corresponding to a strength-duration curve for the chamber on the left side of the patient's heart and determines an initial second controlled energy level accordingly.

22. The implantable cardiac stimulation device of claim 17 wherein:

the controller increases the first controlled energy level in response to a loss-of-capture criteria related to the absence of an evoked response from the right side of the patient's heart; and the controller increases the second controlled energy level in response to a loss-of-capture criteria related to the absence of an evoked response from the left side of the patient's heart.

23. The implantable cardiac stimulation device of claim 17 wherein the stimulation of the left side of the patient's heart by the second stimulation pulse occurs at an interchamber delay period from the stimulation of the right side of the patient's heart by the first stimulation pulse.

24. The implantable cardiac stimulation device of claim 23 wherein the interchamber delay period is set to a delay of essentially 0.0 seconds.

25. The implantable cardiac stimulation device of claim 23 wherein the interchamber delay period is set to cause the right side of the patient's heart to be stimulated prior to the left side of the patient's heart.

26. The implantable cardiac stimulation device of claim 23 wherein the interchamber delay period is set to cause the left side of the patient's heart to be stimulated prior to the right side of the patient's heart.

27. The implantable cardiac stimulation device of claim 25 wherein the right chamber of the patient's heart is the right ventricle and the left chamber of the patient's heart is the left ventricle.

28. The implantable cardiac stimulation device of claim 27 wherein the first electrode is positioned proximate to the right ventricular apex and the second electrode is positioned proximate to the coronary sinus.

29. An implantable cardiac stimulation device configured for stimulating the right and left sides of a patient's heart, the stimulation device comprising:

means for generating first stimulation pulses at a first controlled energy level to thereby stimulate the right side of the patient's heart, wherein the first controlled energy level is defined by a set of characteristics including an amplitude component and a duration component;

first detection means for determining the presence or absence of an evoked response to each of the first stimulation pulses;

means for generating second stimulation pulses at a second controlled energy level to thereby stimulate the left side of the patient's heart, wherein the second controlled energy level is defined by a set of characteristics including an amplitude component and a duration component;

second detection means for determining the presence or absence of an evoked response to each of the second stimulation pulses; and means for adaptively determining the first controlled energy level in response to the first detection means and for adaptively determining the second controlled energy level in response to the second detection means;

a battery to provide power to the implantable cardiac stimulation device; and a voltage detector to detect the present voltage level of the battery; and wherein the controller modifies the amplitude components of the first and second controlled energy levels dependent upon the present battery voltage level and the present first and second amplitude components.

* * * * *